(12) United States Patent
Shirahata et al.

(10) Patent No.: US 8,107,701 B2
(45) Date of Patent: Jan. 31, 2012

(54) MEDICAL IMAGE DISPLAY SYSTEM AND MEDICAL IMAGE DISPLAY PROGRAM

(75) Inventors: Takashi Shirahata, Tokyo (JP); Yoshihiro Goto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 847 days.

(21) Appl. No.: 12/278,505

(22) PCT Filed: Mar. 12, 2007

(86) PCT No.: PCT/JP2007/054792
§ 371 (c)(1),
(2), (4) Date: Aug. 6, 2008

(87) PCT Pub. No.: WO2007/122896
PCT Pub. Date: Nov. 1, 2007

(65) Prior Publication Data
US 2009/0022387 A1    Jan. 22, 2009

(30) Foreign Application Priority Data
Mar. 29, 2006    (JP) ................................. 2006-092173

(51) Int. Cl.
*G06K 9/00* (2006.01)
(52) U.S. Cl. ........................................................ 382/128
(58) Field of Classification Search .................. 382/128, 382/130
See application file for complete search history.

(56) References Cited

U.S. PATENT DOCUMENTS

| | | | | |
|---|---|---|---|---|
| 2006/0285734 A1* | 12/2006 | Haider et al. | ................. | 382/128 |
| 2009/0161927 A1* | 6/2009 | Mori et al. | ..................... | 382/128 |
| 2010/0201683 A1* | 8/2010 | Shirahata et al. | ............. | 345/420 |
| 2011/0066635 A1* | 3/2011 | Moriya | ........................ | 707/769 |

FOREIGN PATENT DOCUMENTS
WO    WO2005/011501 A1    2/2005
(Continued)

OTHER PUBLICATIONS

Etienne, Alex, et al., "'Soap-Bubble' Visualization and Quantitative Analysis of 3D Coronary Magnetic Resonance Angiograms", *Magnetic Resonance in Medicine*, vol. 48, pp. 658-666 (2002).

(Continued)

*Primary Examiner* — Christopher Mahoney
(74) *Attorney, Agent, or Firm* — Cooper & Dunham, LLP

(57) ABSTRACT

A medical image display apparatus of the present invention is used in a medical image display system having a function of preparing three-dimensional image data on a subject including a plurality of luminal organs and displaying the prepared three-dimensional image data on a display (15) as a three-dimensional image. The medical image display apparatus includes a curved-surface creation section (31) which specifies a desired luminal organ in an image showing the plurality of luminal organs displayed on the display (15) and sets a curved surface where the specified desired luminal organ is present; a developed-image creation section (33) which extracts, from the three-dimensional image data, pixel values on the curved surface set by the curved-surface creation section (31), creates curved-surface image data by use of the extracted pixel values on the curved surface, and reconstructs two-dimensional image data (developed image data) from the created curved-surface image data; and a CPU (11) which controls the display (15) so as to display the developed image data reconstructed by the developed-image creation section (33).

18 Claims, 15 Drawing Sheets

FOREIGN PATENT DOCUMENTS

WO WO2006/118100 A1 11/2006

OTHER PUBLICATIONS

Shirahata, Takashi, et al., "Development of coronary visualization algorithm using CPR technique", *Japanese Society of Medical Imaging Technology Annual Meeting*, P2-52 (Aug. 2004); with English translation of Abstract.

Shirahata, Takashi et al., "Kandomyaku CPR Hyoji no Algorithm no Kaihatsu", (256) *Japanese Society of Radiological Technology*, p. 1249 (2004).

\* cited by examiner (a)

(b)

(a)

(b)

(a)

(b)

MEDICAL IMAGE DISPLAY SYSTEM AND MEDICAL IMAGE DISPLAY PROGRAM

TECHNICAL FIELD

The present invention relates to a medical image display system and a medical image display program which display, as information more useful for diagnosis, a plurality of luminal organs contained in a medical image obtained from a medical image capturing apparatus such as an X-ray CT apparatus, an MRI apparatus, or an ultrasonic apparatus.

BACKGROUND ART

A medical image is obtained from a medical image capturing apparatus, and is displayed on a display apparatus. A doctor observes and diagnoses the medical image displayed on the display apparatus. In some cases, the medical image to be observed includes a plurality of luminal organs such as blood vessels, bronchial tubes, and intestines in a complicated form, depending on a portion from which the medical image is captured. A method of observing such luminal organs is disclosed in, for example, Non-Patent Document 1. In the Non-Patent Document 1, a display displays a medical tomographic image captured by means of a medial tomographic image capturing apparatus. By reference to the displayed medical tomographic image, an operator sets, by use of a mouse, a starting point of a region for extracting a luminal organ region to be observed. Through use of a predetermined extraction algorithm, a CPU extracts the luminal organ region from the set starting point, and detects a branching portion of the extracted luminal organ region. The CPU then extracts, through use of the predetermined extraction algorithm, luminal organs extending from the detected branching portion.
Non-Patent Document 1: A. Etienne, R. M. Botnar, A. M. C. Muiswinkel, et al.: Soap-Bubble visualization and quantitative analysis of 3D coronary magnetic resonance angiograms, Magn Reson Med Vol. 48, pp. 658-666 (2002).

DISCLOSURE OF THE INVENTION

Problems to be Solved by the Invention

However, the method disclosed in the above-described Non-Patent Document 1 has a problem which has not yet been solved. When a plurality of luminal organs surrounding an organ are displayed together as a single image, the created image may vary depending on the number and positions of points designated by an operator such as a doctor. Setting of these designation points is likely to be influenced by the skill of the operator, and, for example, using a different operator makes it difficult to reproduce the same image.

An object of the present invention is to provide a medical image display system and a medical image display program which can display a plurality of luminal organs together in the same manner irrespective of who operates the system.

Means for Solving the Problems

A medical image display system according to the present invention has a function of preparing three-dimensional image data on a subject including a plurality of luminal organs and displaying the prepared three-dimensional image data on a display apparatus as a three-dimensional image, and is characterized by comprising curved-surface setting means for specifying a desired luminal organ in an image showing the plurality of luminal organs displayed on the display apparatus and setting a curved surface where the specified desired luminal organ is present; image creation means for extracting, from the three-dimensional image data, pixel values on the curved surface set by the curved-surface setting means, creating curved-surface image data by use of the extracted pixel values on the curved surface, and reconstructing two-dimensional image data from the created curved-surface image data; and display control means for controlling the display apparatus so as to display the two-dimensional image data reconstructed by the image creation means.

A medical image processing program according to the present invention is characterized in that the program causes a computer to execute a function of preparing three-dimensional image data on a subject including a plurality of luminal organs; a function of displaying the prepared three-dimensional image data on a display apparatus as a three-dimensional image; a function of specifying a desired luminal organ in an image of the plurality of luminal organs displayed on the display apparatus; a function of setting a curved surface where the specified desired luminal organ is present; a function of calculating, from the three-dimensional image data, pixel values on the set curved surface; a function of creating curved-surface image data by use of the calculated pixel values on the curved surface; a function of reconstructing two-dimensional image data from the created curved-surface image data; and a function of controlling the display apparatus so as to display the reconstructed two-dimensional image data.

Effects of the invention

According to the present invention, it is possible to provide a medical image display system, a medical image display method, and a medical image display program which can display a plurality of luminal organs together in the same manner irrespective of who operates the system.

DESCRIPTION OF REFERENCE NUMERALS

Figure 1:
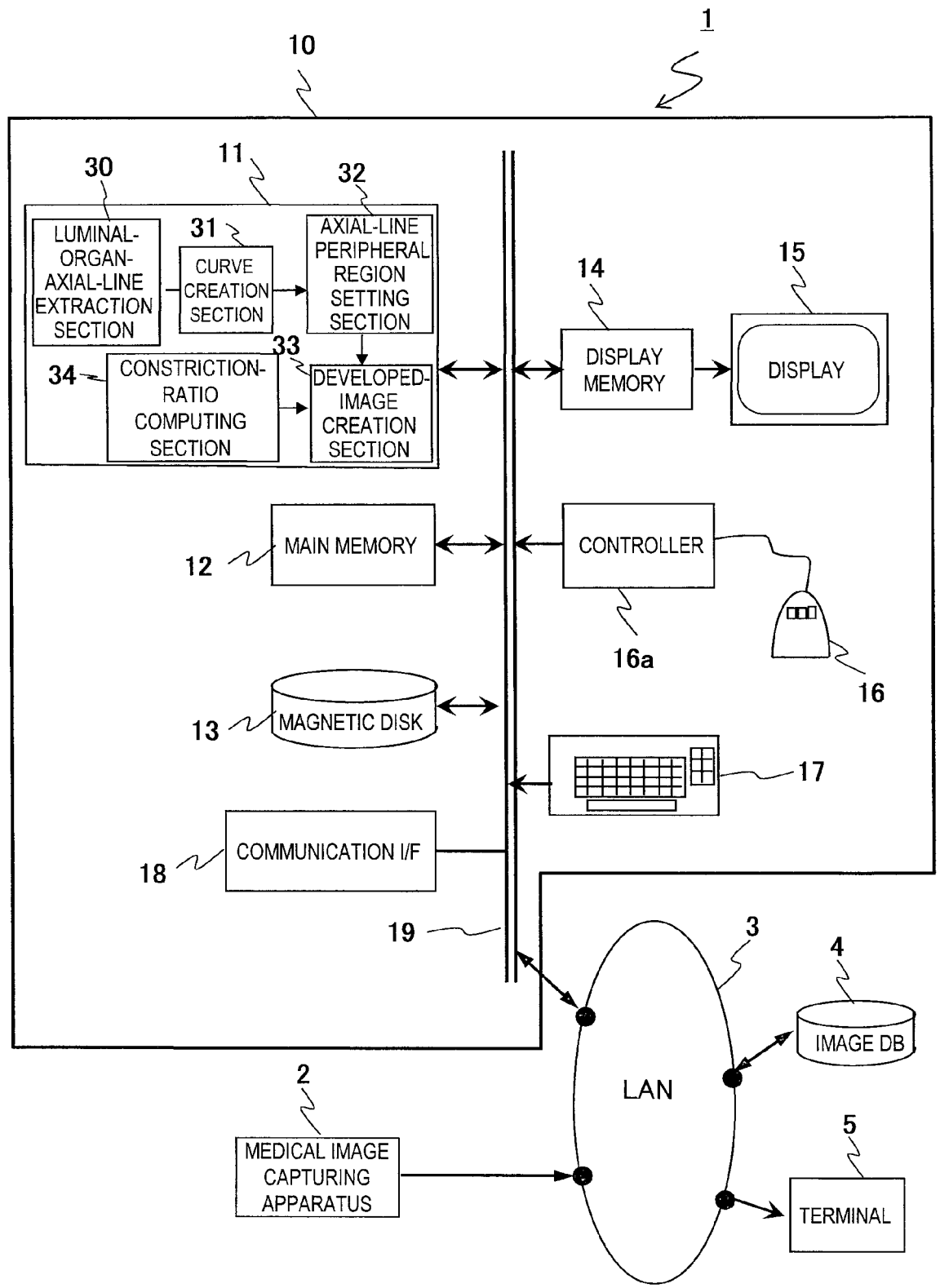
FIG. 1 Hardware configuration diagram showing the configuration of a medical image display system.

1: medical image display system
2: medical image capturing apparatus
3: LAN
4: image DB
5: terminal
10: image display apparatus
11: CPU
12: main memory
13: magnetic disk
14: display memory
15: monitor
16: mouse
16a: controller
17: keyboard
18: communication I/F
19: common bus
30: luminal-organ-centerline extraction section
31: curve creation section
32: centerline peripheral region setting section
33: developed-image creation section
34: constriction-ratio computing section

BEST MODE FOR CARRYING OUT THE INVENTION

The inventors of the present invention describe embodiments thereof with reference to the drawings. FIG. 1 shows an example medical image display apparatus according to the present invention. Notably, in order to describe the embodiments of the present invention, sections having like functions are denoted by like reference numerals throughout the drawings, and their descriptions will not be repeated.
<System Configuration>
FIG. 1 is a hardware configuration diagram showing the configuration of a medical image display system common among the embodiments.

The medical image display system 1 of FIG. 1 includes a medical image capturing apparatus 2, as well as an image data base (image DB) 4 and an image display apparatus 10, which are connected to the medical image capturing apparatus 2 via a local area network (LAN) 3.

The medical image capturing apparatus 2 captures a medical image of a subject. Examples of the medical image capturing apparatus 2 include an X-ray CT apparatus, an MRI apparatus, and an ultrasonic apparatus. However, the medical image capturing apparatus 2 is not limited thereto, and any other apparatus can be selectively used, so long as the selected apparatus can capture a medical image of a subject. The image DB 4 accumulates medical images captured by the medical image capturing apparatus 2. The image display apparatus 10 displays the medical images of the subject. The term "medical image" used herein should be broadly interpreted so as to encompass not only a medical image captured by the medical image capturing apparatus, but also a secondary medical image obtained through image processing of the captured medical image, such as a quasi three-dimensional image or a developed image.

A terminal 5 is connected to the LAN 3 together with the image display apparatus 10, and displays a medical image independently of the image display apparatus 10.

In the image display apparatus 10, a main memory 12, a magnetic disk 13, a display memory 14, a display 15, a controller 16a, a keyboard 17, and a communication interface (hereinafter referred to as "communication I/F") 18 are connected to a central processing unit (CPU) 11 via a common bus 19.

The CPU 11 controls operations of the various components connected to the CPU 11. The main memory 12 stores a control program for the display apparatus, and provides a working area used when the program is executed. The magnetic disk 13 stores an operating system (OS), device drives for peripheral devices, and various application software programs, including a program for creating and displaying a developed image, which will be described later. The magnetic disk 13 also receives, via a network such as the LAN 3, medical images captured by the medical image capturing apparatus 2, and stores them. The display memory 14 temporarily stores data to be displayed. The display 15 is a CRT monitor, a liquid crystal monitor, or a like monitor, which displays an image on the basis of the data from the display memory 14. A mouse 16 is connected to the controller 16a, which transmits information to the CPU 11 via the common bus 19, the information being input by an operator through the mouse 16. The mouse 16 is a device for entering information regarding a position on the screen of the display 15 desired by the operator, and an input command present at the desired position. The keyboard 17 enables the operator not only to enter information regarding the designated position on the screen of the display 15 as in the case of the mouse 16, but also to enter conditions under which the display 15 displays an image or the like. The communication I/F 18 is an interface for connecting the communication bus 19 and the LAN 3. The common bus 19 connects the above-described constituent elements such that they can transfer data mutually.

The CPU 11 of the image display apparatus 10 includes a luminal-organ-centerline extraction section 30; a curve creation section 31 connected to the luminal-organ-centerline extraction section 30; a centerline peripheral region setting section 32 connected to the curve creation section 31; a developed-image creation section 33 connected to the centerline peripheral region setting section 32; and a constriction-ratio computing section 34 connected to the developed-image creation section 33.

The curve creation section 31, the centerline peripheral region setting section 32, and the constriction-ratio computing section 34 are connected to the mouse 16 and the keyboard 17 via the common bus 19. The developed-image creation section 33 is connected to the display memory 14 via the common bus 19.

The luminal-organ-centerline extraction section 30 obtains a plurality of center points of a transverse cross section of each luminal organ, and obtains a line (centerline) by successively connecting adjacent points of the plurality of obtained center points. The centerline obtained by this method assumes a zigzagged shape. The luminal-organ-centerline extraction section 30 may be configured to smoothly connect the center points of the transverse cross section of each luminal organ. The curve creation section 31 forms a curve which connects points (center points) present at corresponding positions on respective centerlines. The centerline peripheral region setting section 32 sets, as a processing region, a small area including the intersection between the curve and each centerline. The developed-image creation section 33 obtains pixel values on the curve, and creates a developed image, which is a single two-dimensional image on which a plurality of luminal organs are depicted. The constriction-ratio computing section 34 detects a contracted portion of a luminal organ designated by use of the mouse 16 or the like, and calculates the constriction ratio thereof.

Various embodiments will now be described with reference to the drawings. Here, the embodiments will be described, by reference to a case where an image of the heart is captured and the coronary artery is a luminal organ to be observed.

<Main Flow Common Among the Embodiments>

Figure 2:
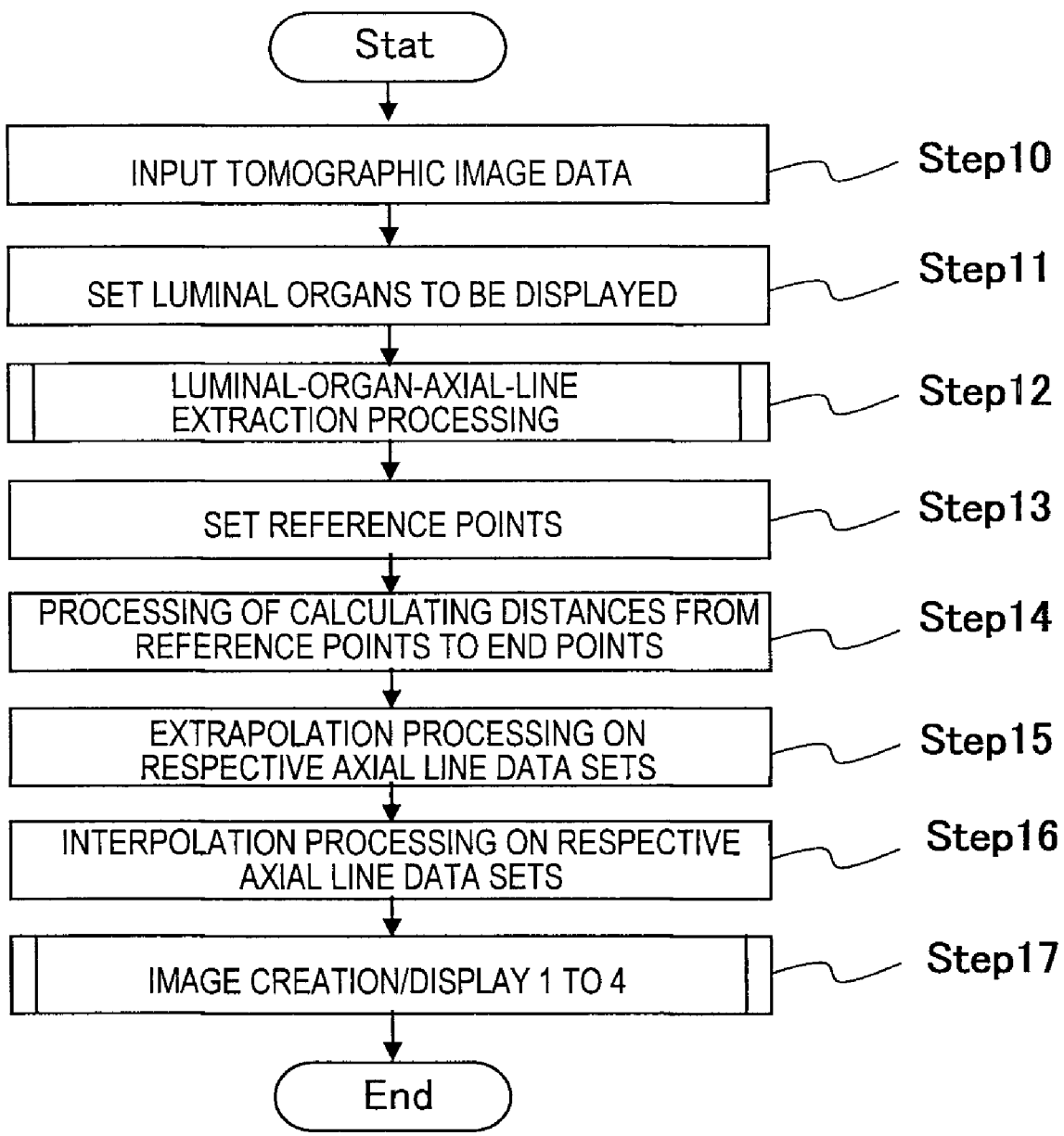
FIG. 2 Example main processing flow common among embodiments of the present invention.
Figure 3:
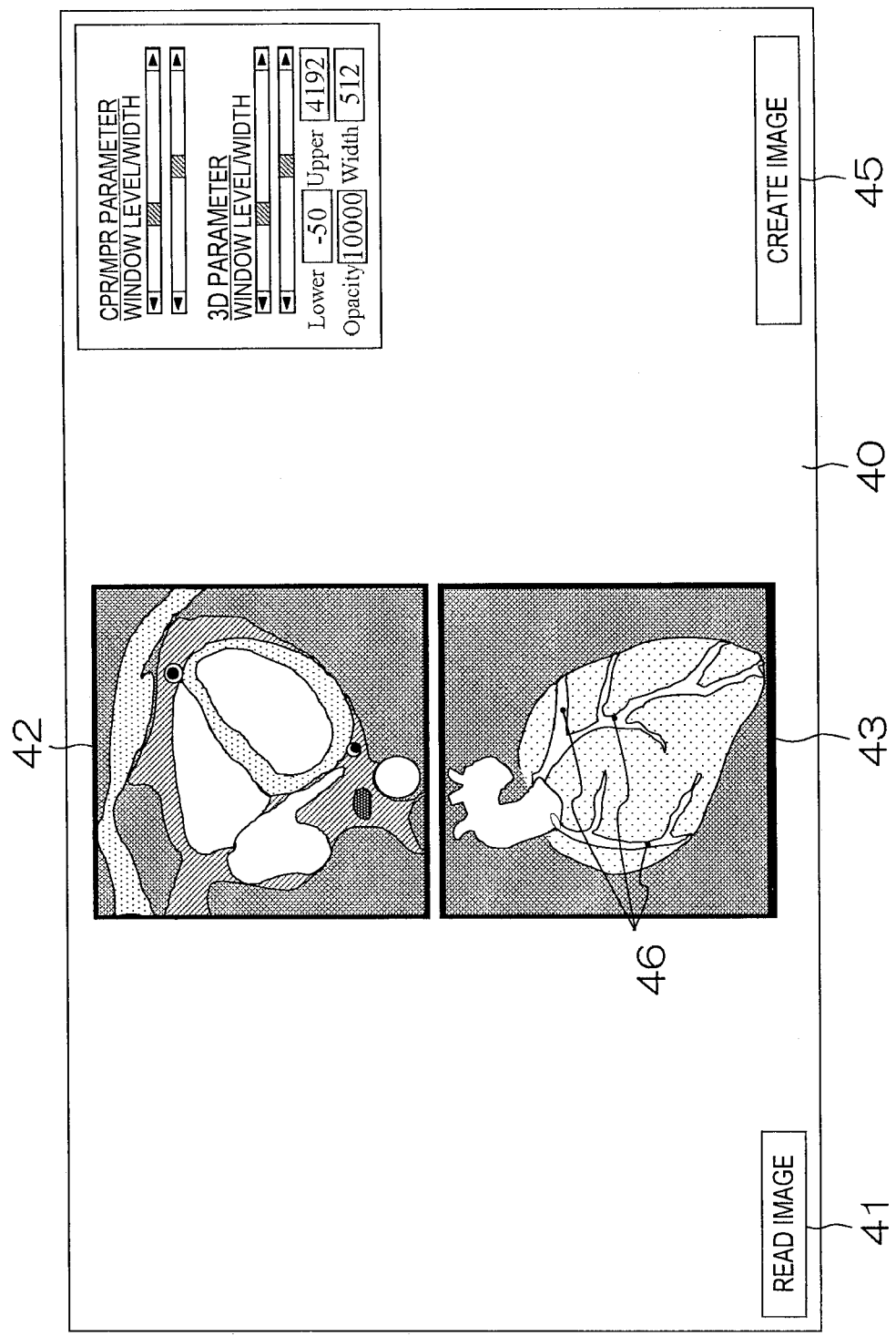
FIG. 3 Example GUI which realizes the embodiments of the present invention.
Figure 4:
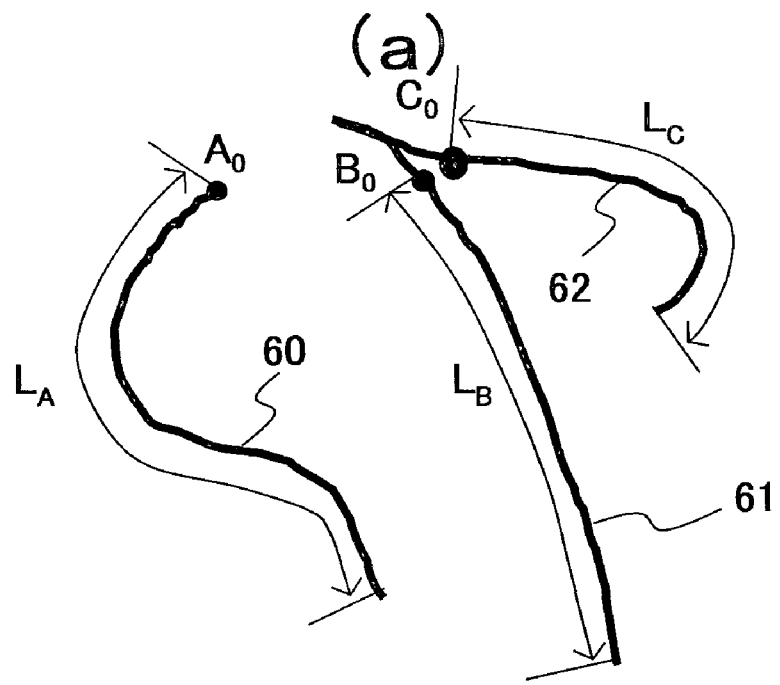
FIG. 4 Schematic diagram used for describing the processing of steps 12 and 15 of FIG. 2.
Figure 4:
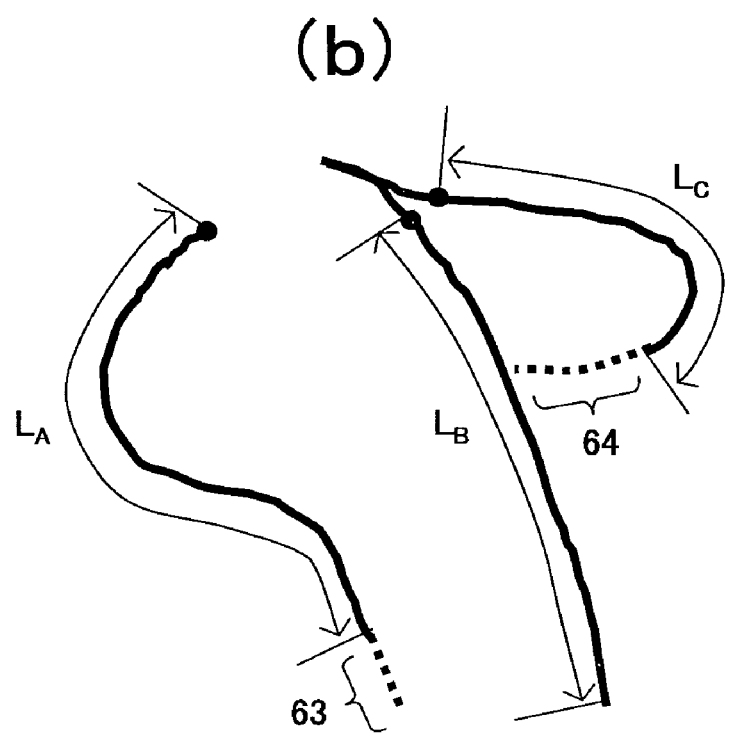
Figure 5:
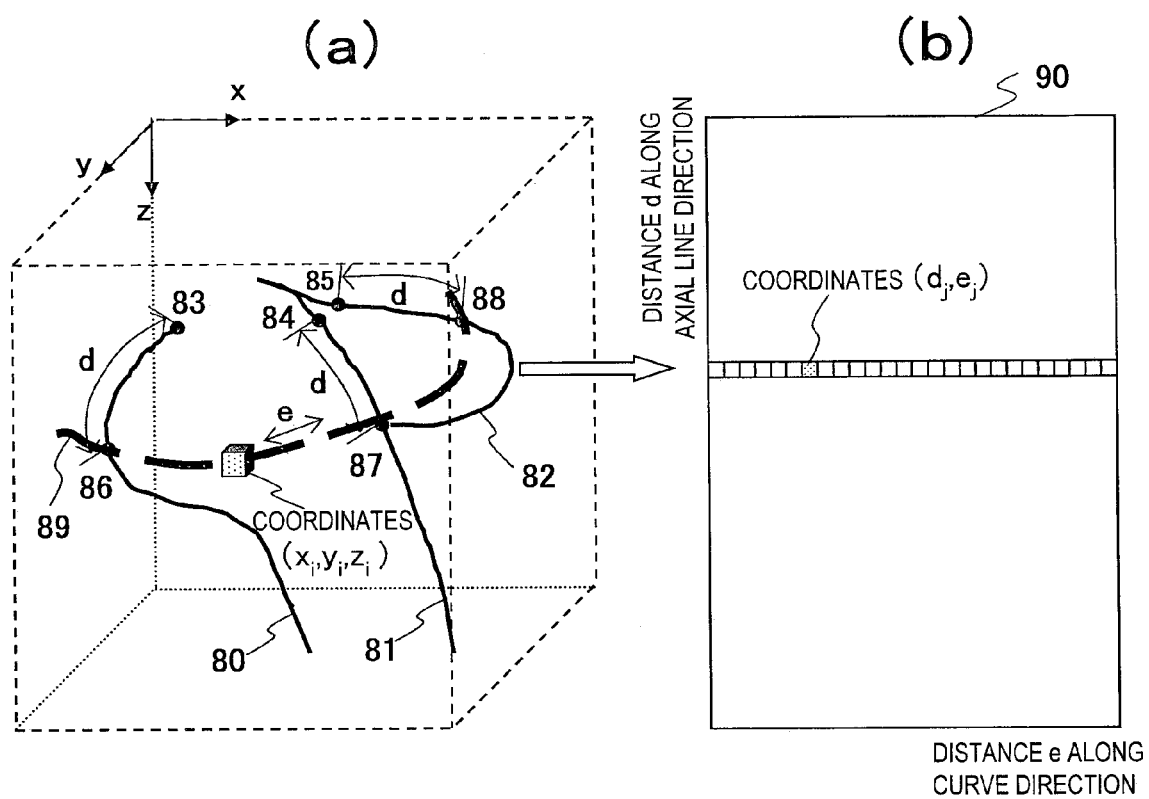
FIG. 5 Schematic diagrams used for describing the interpolation processing of step 16 of FIG. 2.

The main processing common among the embodiments of the present invention will be described with reference to FIGS. 2 to 5. FIG. 2 shows an example main processing flow common among the embodiments. FIG. 3 shows an example GUI (Graphic User Interface) which realizes the first embodiment (including a portion common among the embodiments). FIG. 4 is a schematic diagram used for describing the processing of steps 12 and 15 of FIG. 2. FIG. 5 is a set of schematic diagrams used for describing the processing of step 16 of FIG. 2. First, the individual steps of FIG. 2 will be described below.

(Step 10)

The operator presses an image read button 41 on a GUI 40 of FIG. 3 by operating the mouse 16 so as to transfer from the magnetic disk 13 to the display memory 14 a group of medical tomographic images (a volume image composed of stacked tomographic images) which include a coronary artery area to be observed. The images transferred to the display memory 14 are displayed in image display areas 42 and 43 on the GUI 40 of the display 15. For example, at least two images are displayed in the image display areas 42 and 43. The displayed images may be arbitrarily selected from an axial image, a coronal image, a sagittal image, a surface rendering three-dimensional (3D) image, a volume rendering 3D image, an MPR (Multi Planar Reconstruction) image, and an MIP (Maximum Intensity Projection) image.

(Step 11)

Through operation of an input device such as the mouse 16, the operator designates, one by one, all coronary artery areas to be monitored, from the images displayed in the image display areas 42 and 43 on the GUI 40. Here, the operator designates, one by one, points 46 on the coronary artery areas to be monitored.

(Step 12)

On the basis of the points 46 designated in step 11, the CPU 11 (the luminal-organ-centerline extraction section 30) extracts, from the input images, a curve which passes through the center of each coronary artery area to be observed (hereinafter referred to as "centerline"). A luminal organ area extraction method described in, for example, WO2005/011501 is used as a method for extracting the centerline.

(Step 13)

The CPU 11 (the luminal-organ-centerline extraction section 30) sets reference points as shown in FIG. 4 for the centerlines detected in step 12 (e.g., centerlines 60 to 62 of FIG. 4) by the following method. First, the luminal-organ-centerline extraction section 30 reads the z coordinates at the heads of respective centerline data sets (the upper ends of the centerlines) shown in FIG. 4, and the upper end whose z coordinate is the greatest is selected as a reference point $A_0$. Reference points $B_0$ and $C_0$ on the coronary artery centerlines other than the centerline carrying the reference point $A_0$ are determined such that the reference points $B_0$ and $C_0$ have the same z coordinate value as the reference point $A_0$.

(Step 14)

The CPU 11 (the luminal-organ-centerline extraction section 30) determines a distance $L_i$ along each centerline (i: coronary artery centerlines A, B, C, ... ) from the reference point to the peripheral end point of each coronary artery centerline as shown in FIG. 4. The luminal-organ-centerline extraction section 30 obtains the maximum distance $L_{max}$ from the distances obtained in step 14. In FIG. 4(a), $L_{max}=L_B$.

(Step 15)

For the coronary artery centerlines other than that having the maximum distance $L_{max}$ obtained in step 15, the CPU 11 (the luminal-organ-centerline extraction section 30) changes their lengths such that the distance from the reference point set in step 13 to the peripheral end point becomes equal to $L_{max}$. When the distance from the reference point to the peripheral point is less than $L_{max}$, the CPU 11 performs extrapolation processing for the coronary artery centerlines other than that having the maximum distance $L_{max}$ such that these centerlines are extended over areas 63 and 64 to have a length equal to $L_{max}$ (shown in FIG. 4(b)).

(Step 16)

The CPU 11 (the luminal-organ-centerline extraction section 30) performs interpolation processing such that the distance between adjacent points on the centerlines stored in a centerline data storage array becomes 1, so as to obtain interpolated centerline data.

(Step 17)

The CPU 11 (the developed-image creation section 33) creates an image from the interpolated centerline data, stores the created image in the display memory 14, and displays the stored image on the display 15. In the following embodiments, a subroutine which is called from this step will be described.

FIRST EMBODIMENT

Figure 6:
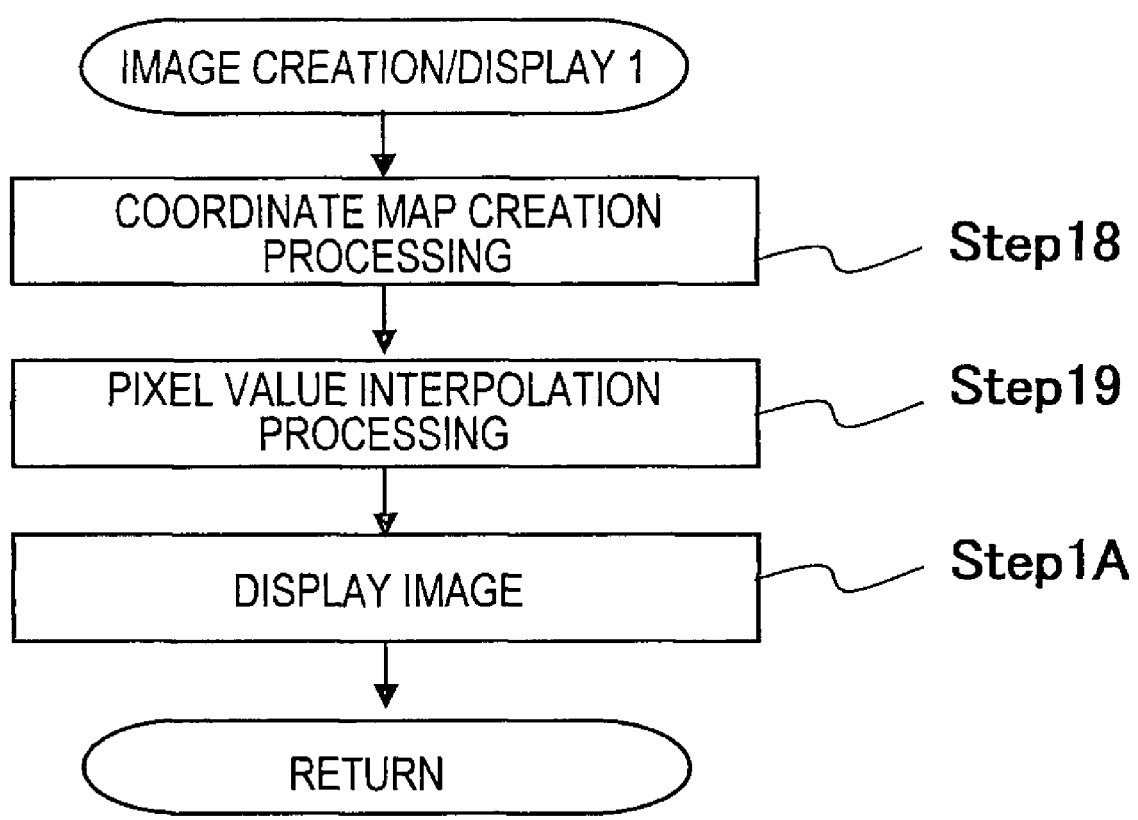
FIG. 6 Example sub-processing flow of a first embodiment.

The first embodiment of the present invention will be described with reference to FIG. 6. FIG. 6 shows an example processing flow of the first embodiment, which is performed subsequent to the processing of FIG. 2. The steps of FIG. 6 will be described below.

(Step 18)

FIG. 5(a) is a schematic diagram showing the centerlines obtained in step 16 in a real space (three-dimensional space).

The CPU 11 (the curve creation section 31) forms a curve which connects a point 86 on a centerline 80, a point 87 on a centerline 81, and a point 88 on a centerline 82, the centerlines being obtained in step 16. The distance d between a reference point 83 and the point 86 of the centerline 80 is equal to the distance d between a reference point 84 and the point 87 of the centerline 81 and the distance d between a reference point 85 and the point 88 of the centerline 82. This curve is obtained through curve approximation (for example, a curve 89 shown in FIG. 5(a)). The approximation curve 89 may be a spline curve, a cubic curve, or a Bezier curve. Next, the CPU 11 obtains coordinates $(x_i, y_i, z_i)$ of each point on the approximation curve 89 in the three-dimensional coordinate space. Here, the coordinates in the three-dimensional coordinate space refer to those in a coordinate system represented by coordinate axes x, y, z shown in FIG. 5(a). The CPU 11 relates coordinates $(d_j, e_j)$ of each pixel of an image developed along the approximation curve 89 to the coordinates $(x_i, y_i, z_i)$ of each point on the approximation curve 89. The CPU 11 repeats the operation of relating the coordinates of each pixel of the developed image to the coordinates of each point on the approximation curve, from the reference point to the peripheral end of each coronary artery centerline, to thereby generate a two-dimensional coordinate map 90 (FIG. 5(b)). The two-dimensional coordinate map 90 is configured such that the coordinates $(x_i, y_i, z_i)$ on the curve 89 in the three-dimensional coordinate space are related to the coordinates $(d_j, e_j)$ in the two-dimensional coordinate map 90 by means of the vertical axis and the horizontal axis. That is, the vertical axis represents the distance (distance d along the centerline direction) along the running directions of the centerlines 80 to 82 from the reference points 83 to 85 (i.e., the luminal organs), and the horizontal axis represents the coordinate position along the approximation curve 89 (distance e along the curve direction).
(Step 19)

The CPU 11 (the curve creation section 31) obtains, through interpolation processing, pixel values corresponding to the coordinates at each point on the coordinate map from the group of medical tomographic images input in step 10, and stores the pixel values in a created image data storage array (pixel value line). By virtue of this operation, the extracted approximation curve 89 allows creation of a curved surface passing through all the designated points.
(Step 1A)

Figure 7:
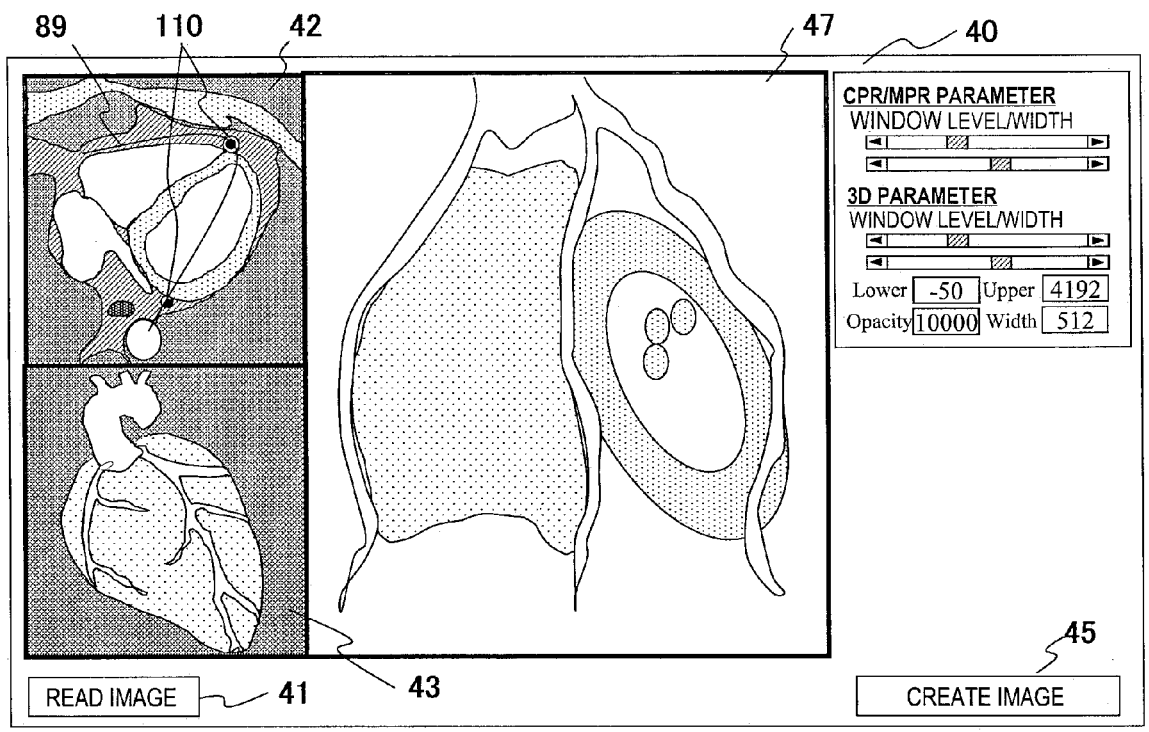
FIG. 7 Example display of a developed image according to the first embodiment.

The CPU 11 (the developed-image creation section 33) displays the image stored in the created image data storage array; i.e., the developed image in an image display area 47 on the GUI 40 (FIG. 7). The image may be displayed in a gray scale, or in such a manner that color values are superposed on gray scale values. This developed image includes a sectional image of the plurality of luminal organs selected in step 11, as taken along the curved surface.

According to the present embodiment, upon designation of a plurality of luminal organs desired to be observed, a developed image can be created and displayed such that the designated luminal organs are displayed on a single two-dimensional image. Thus, in a case where the same volume image is read and the same luminal organs are designated, the same developed image can be obtained each time regardless of who operates the apparatus. Therefore, a developed image can be obtained consistently irrespective of the skill of the operator.

SECOND EMBODIMENT

In step 18 of the first embodiment, a spline curve, a cubic curve, a Bezier curve, or the like is used as a curve which connects a plurality of coronary arteries so as to generate a coordinate map. In a second embodiment, the operator changes on the GUI 40 the set approximation curve connecting the plurality of coronary arteries by use of the mouse 16.

Figure 8:
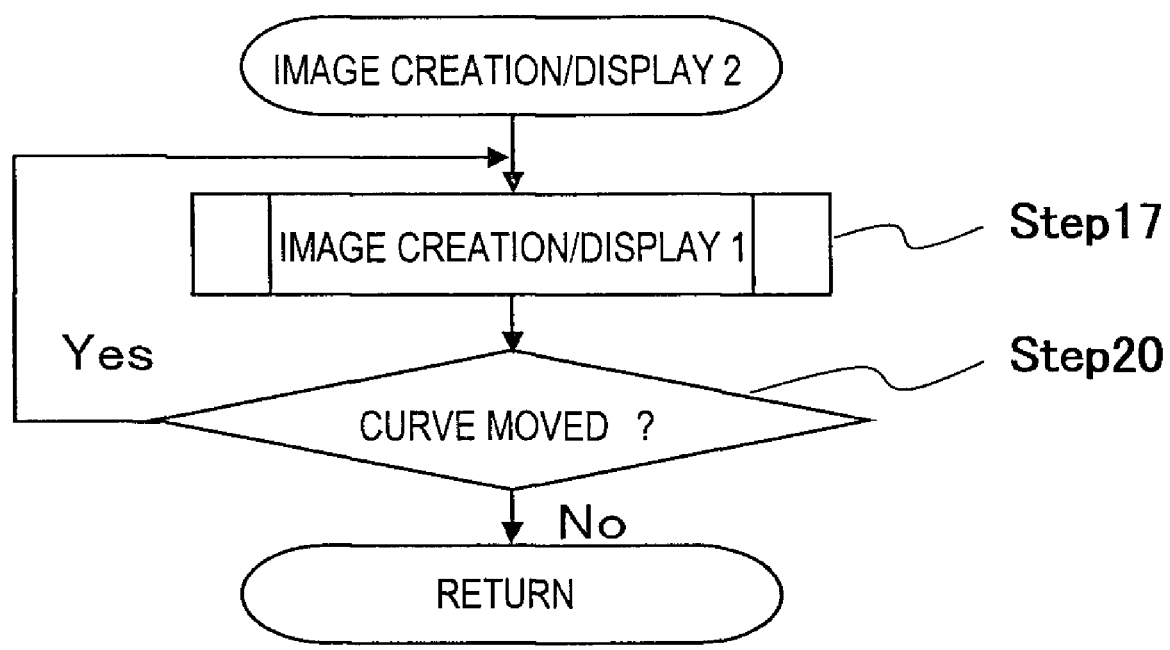
FIG. 8 Example sub-processing flow of a second embodiment.

FIG. 8 is a flowchart showing the flow of processing of the second embodiment. Since the processing in steps 10 to 1A is identical with that of the first embodiment, only a point of difference will be described, without repeating the same description.
(Step 20)

Figure 9:
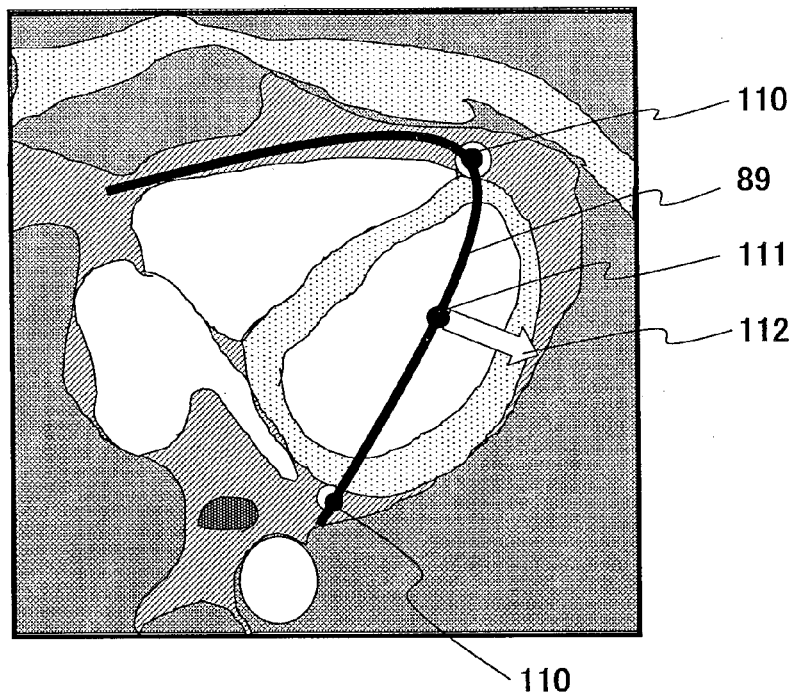
FIG. 9 Schematic diagrams used for describing the processing of the second embodiment.
Figure 9:
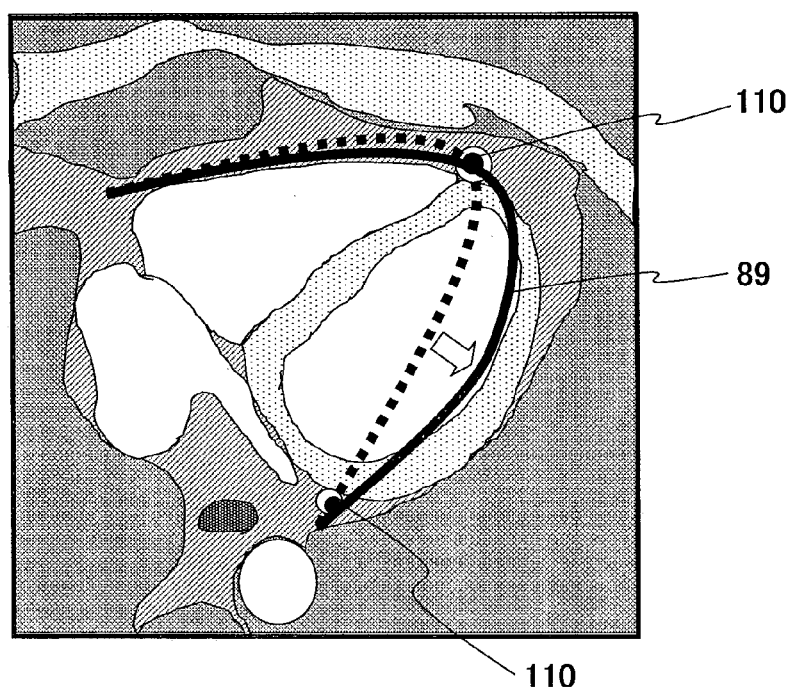

In step 20, the operator performs processing for correcting the position of the approximation curve 89. The arbitrary approximation curve 89 obtained in step 18 is superposed on the heart images displayed in the image display areas 42 and 43 of the GUI 40. FIGS. 9(*a*) and 9(*b*) are example screen displays showing the state where the approximation curve 89 is superposed on the heart image. Notably, FIGS. 9(*a*) and 9(*b*) show only the image displayed in the image display area 42 of the GUI 40 shown in FIG. 7, on which the approximation curve 89 is superposed. However, the images of FIGS. 9(*a*) and 9(*b*) are displayed in a portion of the GUI 40 of FIG. 7.

The operator selects an arbitrary point 111 on the curve by use of the mouse 16. The operator can freely move the curve 89 by dragging the selected point 111 in a direction of an arrow 112. At that time, intersections 110 between the curve 89 and the coronary artery centerlines are prevented from moving. FIG. 9(*a*) shows the approximation curve 89 before its shape has not yet been changed, and FIG. 9(*b*) shows the approximation curve 89 after its shape has been changed. As shown in FIG. 9(*b*) as well, the approximation curve 89 whose shape has been changed passes through the point 110. Since the positions of the intersections between the approximation curve 89 and the centerlines do not change even after the shape of the curve has been changed, no change arises in the distance between the luminal organs in a developed image to be generated later. When the shapes of a plurality of arbitrary curves obtained as the approximation curve 89 are changed and then an image creation button 45 is pressed, the CPU 11 automatically changes the shapes of curves whose shapes were not changed through interpolation. The CPU 11 generates the coordinate map 90 by use of the group of curves obtained here.

According to the present embodiment, a developed image which passes through a portion designated by a user can be created while the positional relation between the luminal organs can be maintained. For example, the user can drag, by use of the mouse 16, the approximation curve 89 which passes through the interior of the heart as shown in FIG. 9(*a*) so as to deform the approximation curve 89 to a shape extending along the outer circumference of the heart as shown in FIG. 9(*b*), to thereby generate a developed image along the outer circumference of the heart.

THIRD EMBODIMENT

In a third embodiment, a small processing region is defied around each centerline, and processing based on an MIP method is performed for this processing region.

Figure 10:
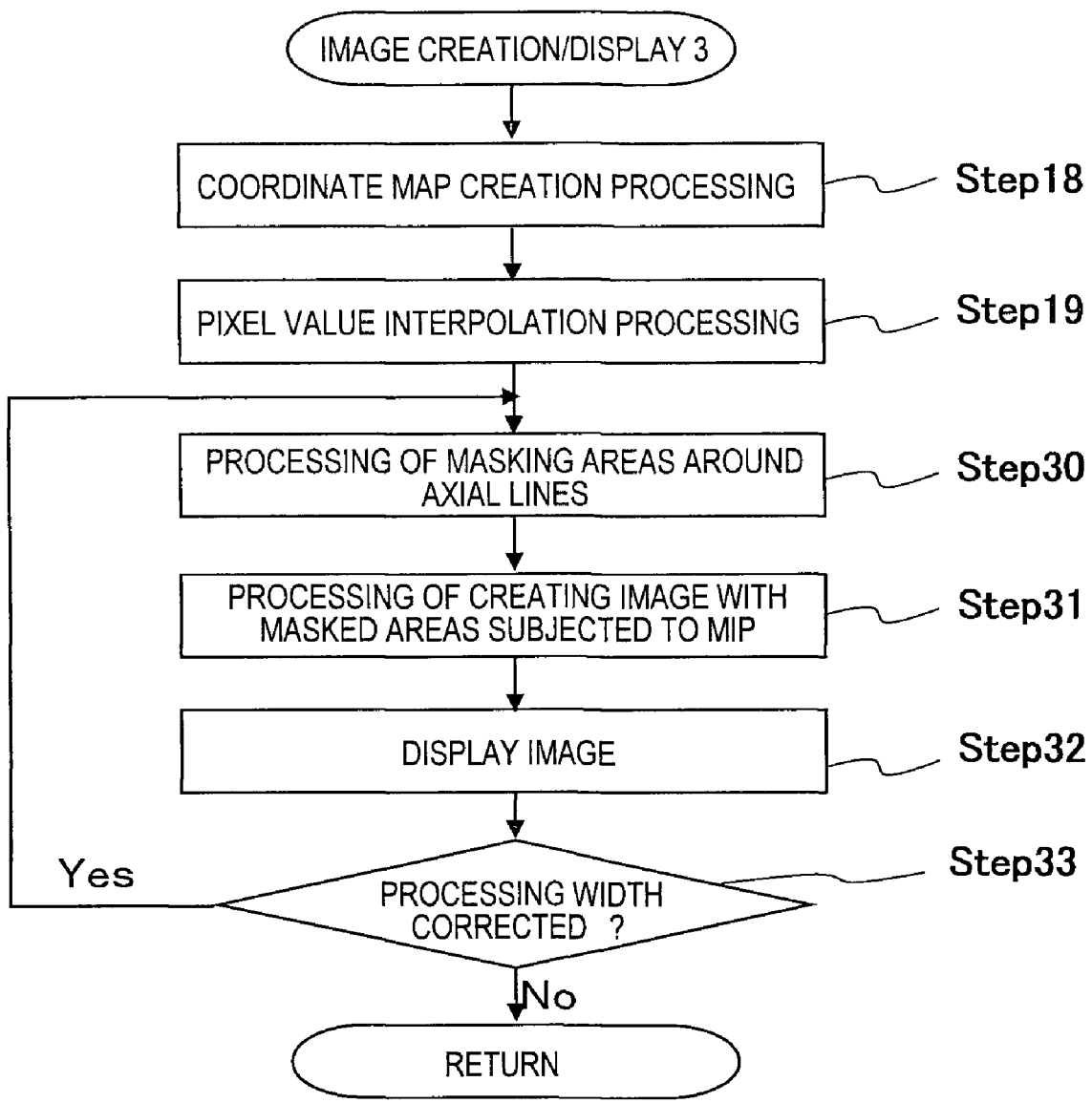
FIG. 10 Example sub-processing flow of a third embodiment.

FIG. 10 is a flowchart showing the flow of processing of the third embodiment. Since the processing in steps 10 to 19 is identical with that of the first embodiment, only a point of difference will be described, without repeating the same description.
(Step 30)

Figure 11:
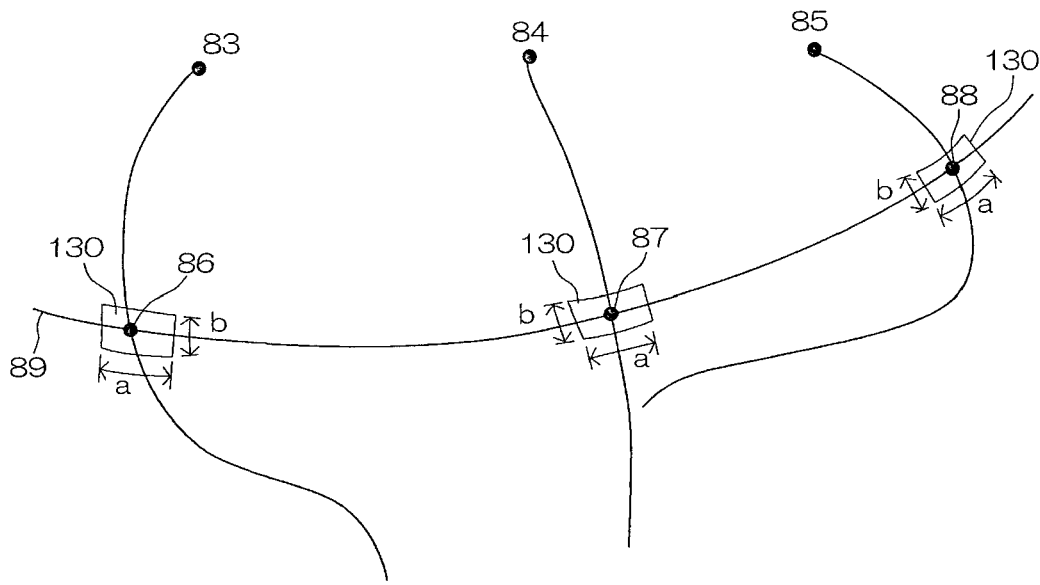
FIG. 11 Schematic diagrams used for describing processing regions in the third embodiment.
Figure 11:
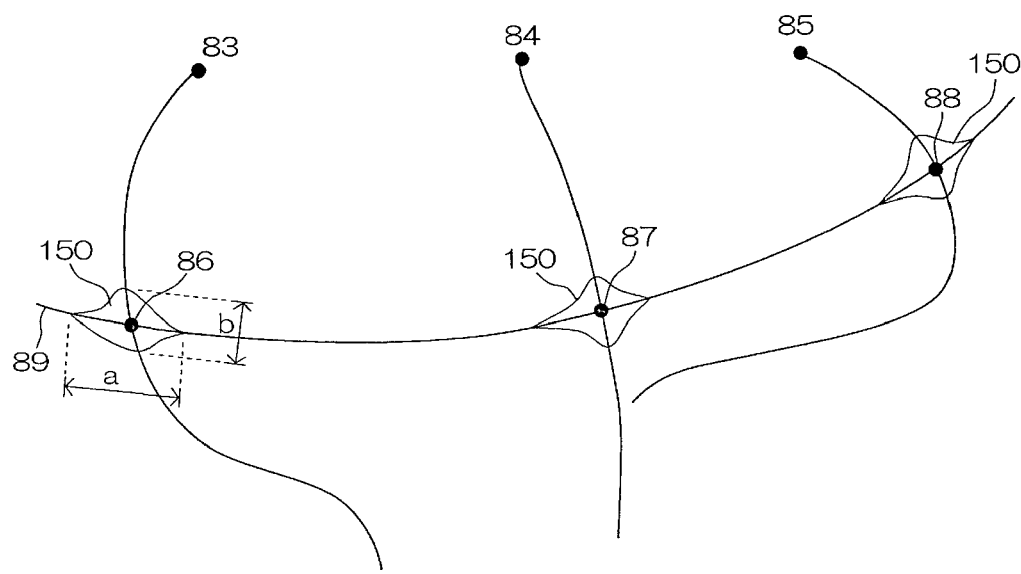

On the two-dimensional map 90, the CPU 11 (the centerline peripheral region setting section 32) imparts a mask value to each processing region 130 having a width a and extending to equal distances in opposite lateral directions from each of the coronary artery centerlines extracted in step 12. FIG. 11 is a pair of schematic diagrams used for explaining processing regions (masked regions) 130. Each of the processing regions 130 is set as a rectangular area which includes the corresponding coronary artery centerline and which has a width a and a height b. The width a and the height b may be previously set values. Alternatively, the apparatus may be configured to enable the operator to input the width a and the height b on the GUI 40 by operating the mouse 16, the keyboard 17, or the like. Preferably, the width a is approximated to an assumed width (diameter) of the coronary artery.
(Step 31)

Of the pixel values stored in the created image data storage array in step 19, the CPU 11 (the centerline peripheral region setting section 32) replaces the pixel values within the masked regions set in step 30 with the result of the processing by the MIP method. The masked regions may be maintained at fixed positions through a single operation or moved along the blood vessels. A projection thickness over which the processing by the MIP method is performed may be a previously set value. Alternatively, the apparatus may be configured to allow the operator to freely set the thickness.
(Step 32)

The CPU 11 (the developed-image creation section 33) displays a developed image in an image display area 47 on the GUI 40, the developed image being the image stored in the created image data storage array and partially replaced with the result of the processing by the MIP method in step 31. The developed image may be displayed in such a manner that color values are superposed on gray scale values in the region in which the processing by the MIP method was performed. Alternatively, only the peripheral edge of the region in which the processing by the MIP method was performed is surrounded by color values.

According to the present embodiment, since the processing by the MIP method can be performed only for regions around the centerlines, a muscle region and other regions separated away from the centerlines are displayed on a developed image without being influenced by the processing by the MIP method. Further, it is possible to prevent a problematic event which would otherwise occur due to some causes; for example, when the shape of the approximation curve 89 is changed as in the second embodiment, and in which the displayed developed image shows a luminal organ as being constricted, even through the luminal organ is not constricted in actuality. Therefore, when the muscle region has an anatomical meaning, such an anatomical meaning is not lost. In addition, a portion which is not constricted is not displayed as being constricted.

Figure 12:
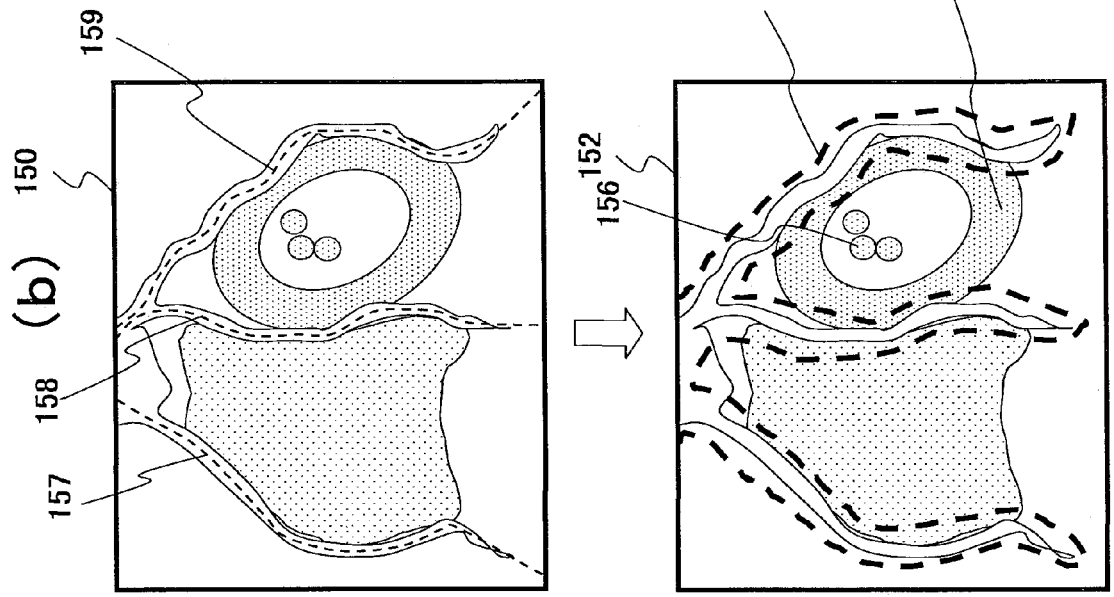
FIG. 12 Example screen displays of a developed image obtained in the third embodiment.
Figure 12:
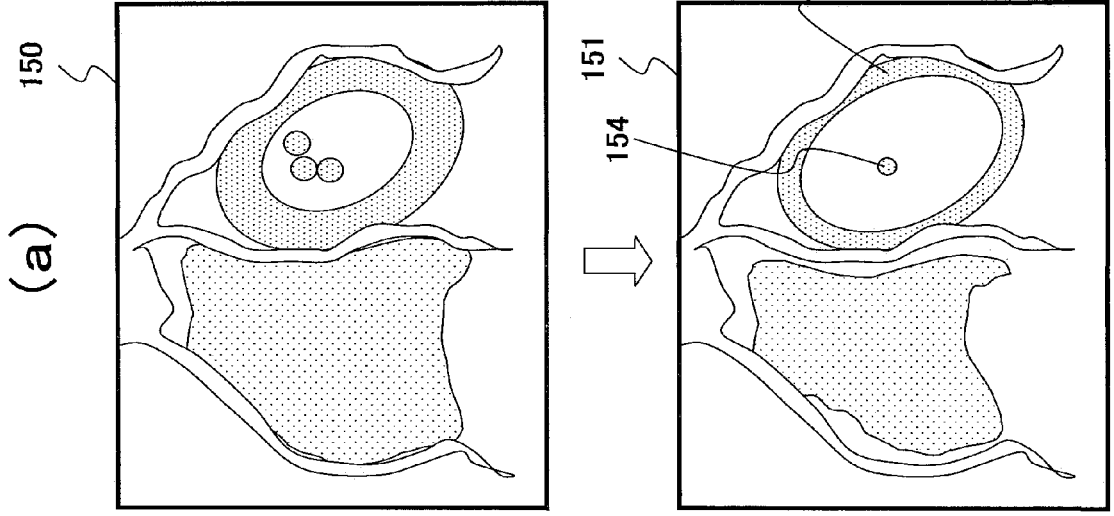

FIG. 12 is an example screen display used for describing a merit of a developed image displayed in the present embodiment. An image 150 is a developed image 150 obtained in the first embodiment. A developed image 151 is obtained by performing the processing based on the MIP method for the entirety of the developed image 150. Further, a developed image 152 is a developed image obtained in the present embodiment.

Luminal organs including centerlines 157, 158, and 159 are displayed on the developed images 151 and 152. The luminal organ of the developed image 151, which is obtained by performing the processing based on the MIP method for the entirety of the developed image 150, is displayed such that it has a higher gradation with respect to the width (diametrical) direction (the running direction of the approximation curve 89), as compared with the developed image 150. Therefore, constriction, plaque, etc. can be readily observed. However, the cardiac muscle 153 and the papillary muscle 154 are displayed in sizes smaller than the actual sizes, or in some cases are not displayed, due to influence of high pixel values of the contrasted blood vessels around the cardiac muscle 153 and the papillary muscle 154. However, the cardiac muscle and the papillary muscle serve as a clue to determine a constricted portion of the blood vessel, and therefore, have an important anatomical meaning.

By contrast, in the developed image 152, the processing based on the MIP method is performed only for the region 160 around the centerlines 157, 158, and 159. Therefore, for the blood vessel, information of the thickness direction is reflected on the image, so that constriction, plaque, etc. can be observed. Further, since the cardiac muscle 155 and the papillary muscle 156 are displayed in correct sizes, their anatomical meaning is not impaired.

FIG. 11(b) shows a variation of the present embodiment. Processing regions 150 of FIG. 11(b) differ in shape from the processing regions 130 of FIG. 11(a). Although the width a of each processing region 150 is equal to the width a of the processing region 130 of FIG. 11(a), the height b is set such that height becomes the largest near the centerline 83, 84, 85, and decreases toward opposite end portions of the processing region 150; i.e., with the distance from the centerline 83, 84, 85. Thus, each processing region 150 generally assumes the shape of a rhombus. By virtue of this, it is possible to prevent generation of a discontinuity in an image at a boundary between a region in which the processing based on the MIP method is performed and a region in which the processing based on the MIP method is not performed. Therefore, an image of higher quality can be obtained.

Notably, in the present embodiment and its variation, the processing based on the MIP method is performed in set processing regions. However, other image processing methods may be performed in accordance with the characteristics of the pixel values in the subject area. For example, for image data of a contrasted blood vessel obtained by use of an X-ray CT apparatus, performing the processing based on the MIP method is desired, because the pixel values of the contrasted blood vessel, which is a subject area, become large. Further, for image data obtained by use of an MRI apparatus or the like such that the pixel values of a subject area are made smaller, performing processing based on minimum intensity projection (MinIP) is desired.

FOURTH EMBODIMENT

In a fourth embodiment, display is performed in such a manner that, of a plurality of to-be-observed coronary arteries displayed on a developed image, an arbitrary one is developed to extend straight.

Figure 13:
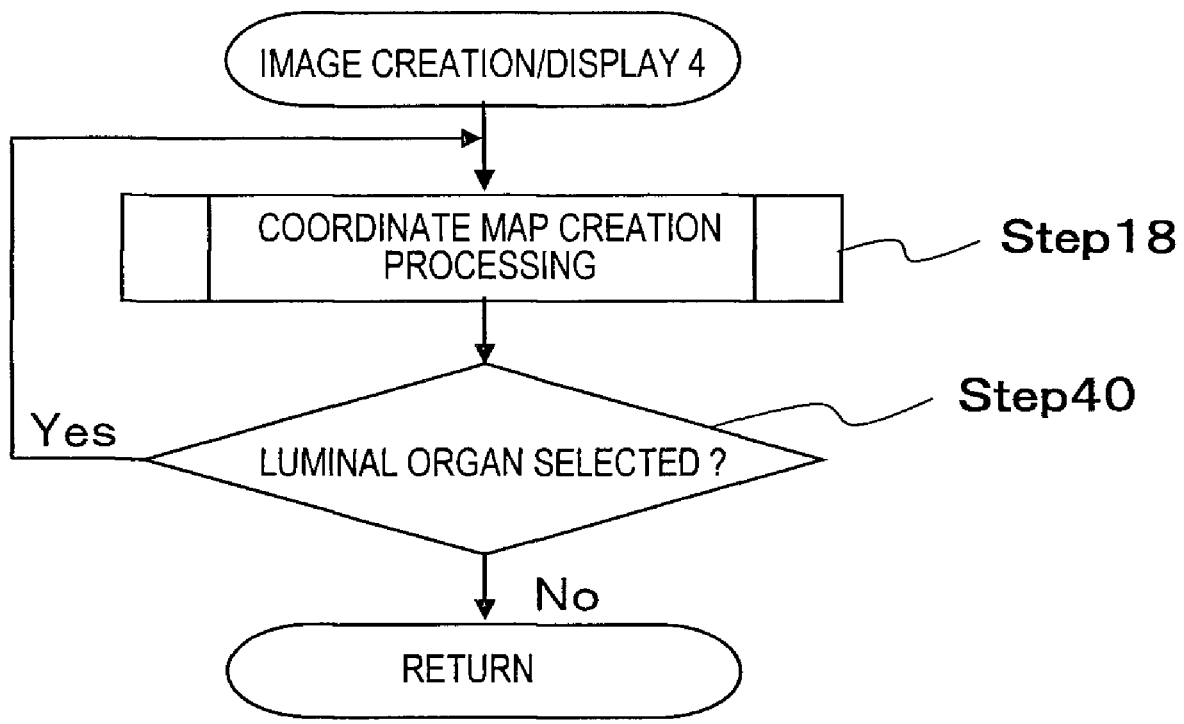
FIG. 13 Example sub-processing flow of a fourth embodiment.

FIG. 13 is a flowchart showing the flow of processing of the fourth embodiment. Since the processing in steps 10 to 1A is identical with that of the first embodiment, only a point of difference will be described, without repeating the same description.

(Step 40)

Figure 14:
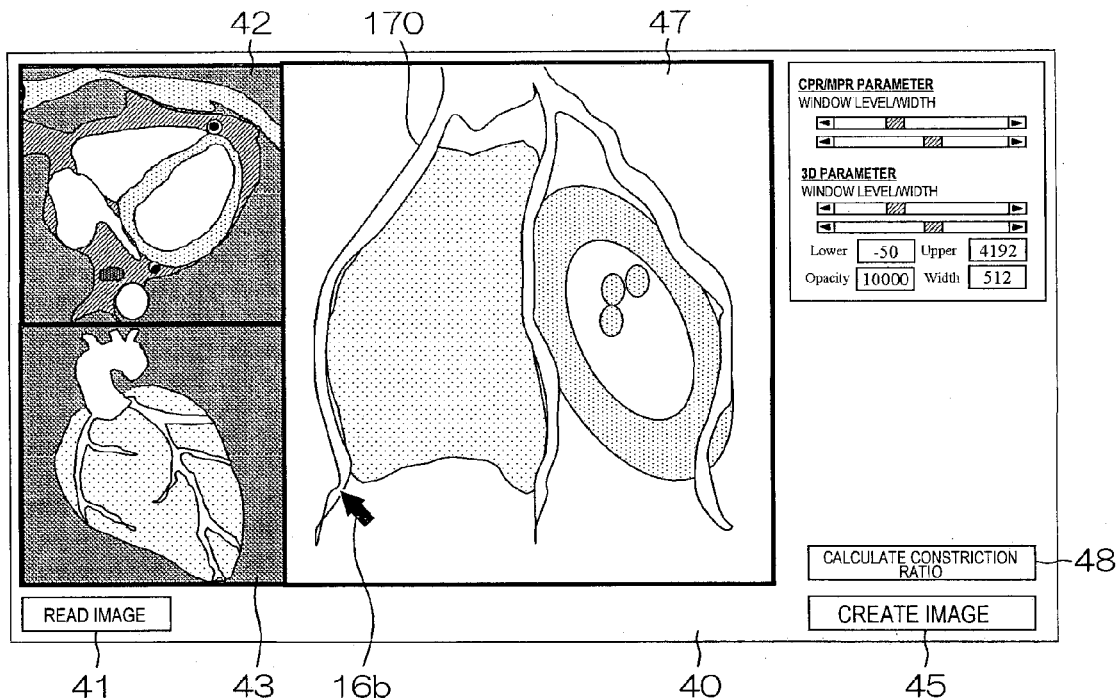
FIG. 14 Example GUI which realizes the fourth embodiment.
Figure 14:
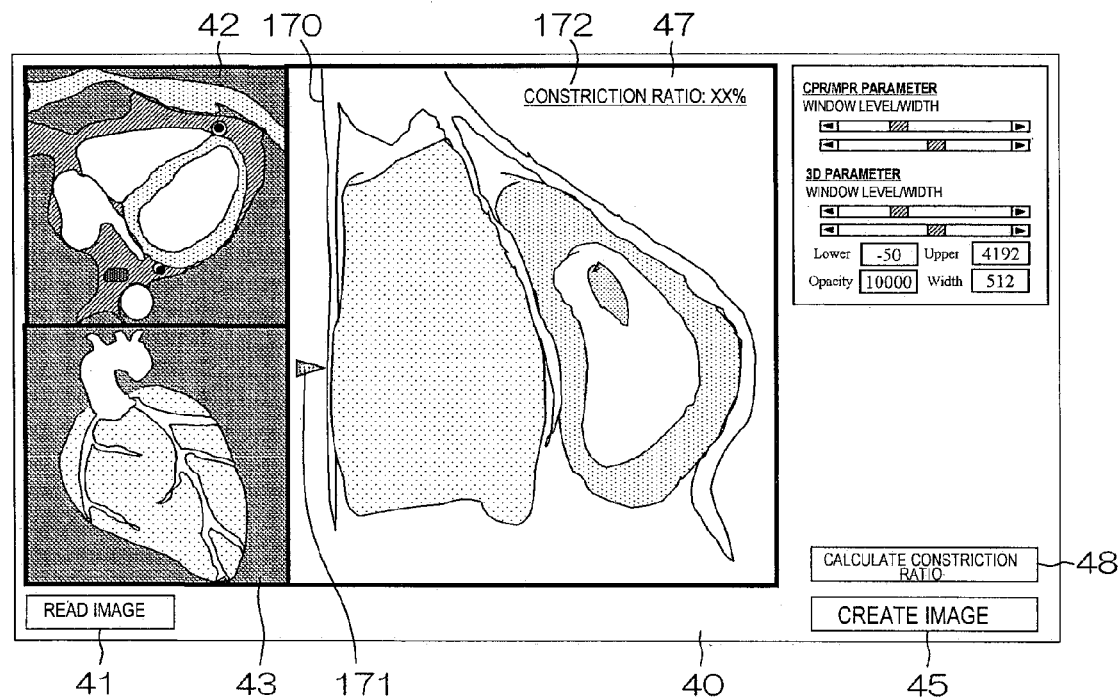
Figure 15:
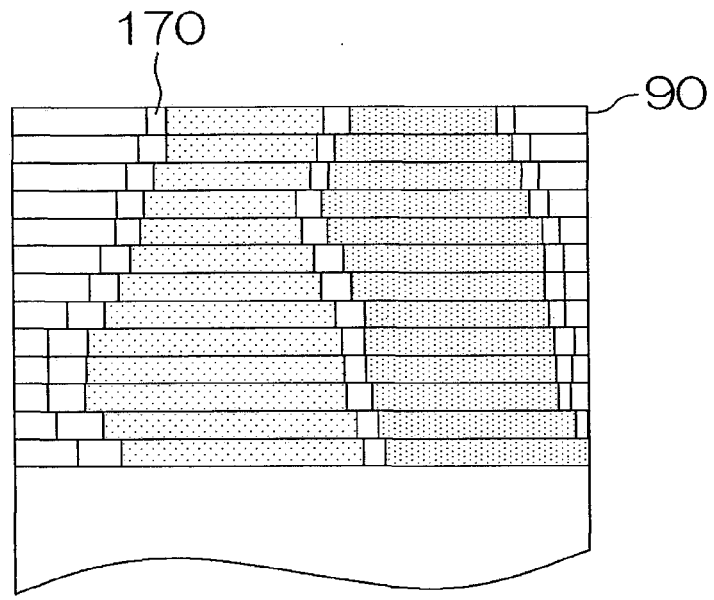
FIG. 15 Example two-dimensional coordinate maps corresponding to the developed images of FIG. 14.
Figure 15:
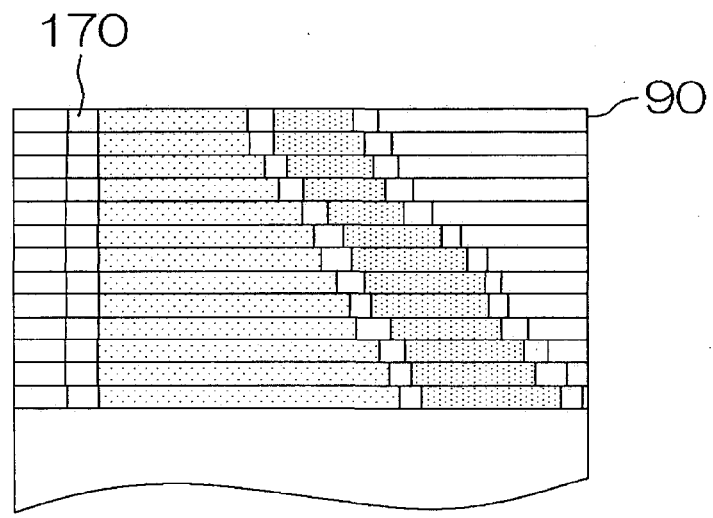

When the operator moves a mouse cursor 16b to an arbitrary point on a single coronary artery 170 contained in a developed image displayed in the image display area 47 shown in FIG. 14(a) and clicks the mouse, the processing flow returns to step 18 of FIG. 6. FIG. 15 is a pair of schematic diagrams showing the details of the processing which the CPU 11 (the developed-image creation section 33) performs upon return to step 18. FIG. 15(a) shows a two-dimensional coordinate map 90 corresponding to the developed image of FIG. 14(a). In FIG. 15(a), the pixels of the coronary artery 170 are disposed in a meandering manner. As shown in FIG. 15(b), the CPU 11 (the developed-image creation section 33) disposes the pixels of the coronary artery 170 straight. If a point(s) which partially defines the approximation curve 89 becomes unavailable as a result of the pixels of the coronary artery 170 being disposed straight, the CPU 11 interpolates the coordinates of the respective points (step 18), obtains their pixel values (step 19), and displays a developed image on the basis of the two-dimensional coordinate map 90 rearranged as a result of this processing (step 1A). FIG. 14(b) shows an example developed image in which the coronary artery 170 is displayed straight. By means of displaying the subject coronary artery straight, visual determination as to whether or not constriction is present is facilitated.

Further, when the operator clicks a constriction-ratio calculation icon 48 shown in FIG. 14(a), the CPU 11 determines whether or not a constricted portion is present on the coronary artery 170. If a constricted portion is present, the CPU 11 may display a marker 171 indicating the constricted portion, and provide a display "CONSTRICTION RATIO: xx %" 172. The constriction ratio may be calculated by use of an existing calculation method, such as a geometric method, or a densitometric metric method. This calculation processing is executed by the constriction-ratio computing section 34.

With this operation, the position and constriction ratio of a constricted portion can be grasped more easily.

According to the above-described embodiments, a plurality of luminal organs to be observed can be displayed on a single image, without requiring operator's troublesome operation. Further, when the processing based on the MIP method is performed for the luminal organs, overlooking of candidate anomalies such as constriction, calcification, and plaque is expected to decrease. Further, peripheral organs do not lose their anatomical position information due to, for example, the processing based on the MIP method, so that the positional relation of the observed organs can be readily grasped.

In the above-described embodiments, an example case where the coronary artery is observed has been described. However, the present invention can be applied to luminal organs other than the coronary artery, such as blood vessels at an arbitrary portion (e.g., lower limb blood vessels or basilar blood vessels), bronchial tubes, and intestinal tract.

Preferred embodiments of the medial image display system according to the present invention have been described. However, the present invention is not limited to the above-described embodiments. It is clear that a person with ordinary skill in the art can easily conceive various modifications and changes within the technical idea disclosed herein, and it is contemplated that such modifications and changes naturally fall within the technical scope of the present invention.

The invention claimed is:

1. A medical image display system having a function of preparing three-dimensional image data on a subject including a plurality of luminal organs and displaying the prepared three-dimensional image data on a display apparatus as a three-dimensional image, the system being characterized by comprising:
    curved-surface setting means for specifying a desired luminal organ in an image showing the plurality of luminal organs displayed on the display apparatus and setting a curved surface where the specified desired luminal organ is present;
    image creation means for extracting, from the three-dimensional image data, pixel values on the curved surface set by the curved-surface setting means, creating curved-surface image data by use of the extracted pixel values on the curved surface, and reconstructing two-dimensional image data from the created curved-surface image data; and
    display control means for controlling the display apparatus so as to display the two-dimensional image data reconstructed by the image creation means.

2. A medical image display system according to claim 1, wherein the curved-surface setting means is connected to luminal-organ-centerline extraction means, wherein the luminal-organ-centerline extraction means obtains a plurality of center points of a transverse cross section of each luminal organ and successively connects adjacent points of the plurality of obtained center points to thereby obtain a centerline; and the curved-surface setting means forms a curve which connects points (center points) located at corresponding positions on the obtained centerlines.

3. A medical image display system according to claim 2, wherein the image creation means is connected to centerline peripheral region setting means, wherein the centerline peripheral region setting means sets, as a processing region, a small area including an intersection between each centerline and the curve set by the curved-surface setting means; and the image creation means obtains pixel values on the curve, and creates a developed image in which the plurality of luminal organs are depicted on a single two-dimensional image.

4. A medical image display system according to claim 2, wherein the luminal-organ-centerline extraction means creates a plurality of centerlines passing through the radial centers of the plurality of selected luminal organs, and calculates, from the plurality of created centerlines, designation points used for creating the curve.

5. A medical image display system according to claim 2, wherein the luminal-organ-centerline extraction means creates a plurality of centerlines passing through the radial centers of the plurality of selected luminal organs, sets a reference point for each of the plurality of created centerlines, and calculates designation points used for creating the curve, at predetermined intervals along the centerlines from the reference points.

6. A medical image display system according to claim 2, wherein the luminal-organ-centerline extraction means creates a plurality of centerlines passing through the radial centers of the plurality of selected luminal organs, and calculates new interpolation points by performing interpolation processing while using arbitrary points which constitute the plurality of created centerlines, the new interpolation points serving as designation points used for creating the curve.

7. A medical image display system according to claim 2, further comprising region setting means for setting processing regions including intersections between the plurality of centerlines created by the luminal-organ-centerline extraction section and the curved surface created by the curved-surface setting means, wherein the image creation means uses, in place of pixel values of the three-dimensional image data at each point within the set processing region, pixel values calculated by performing at least one of maximum intensity projection processing and minimum intensity projection processing on pixel values of the three-dimensional image data in the vicinity of the point within the processing region.

8. A medical image display system according to claim 7, wherein the region setting means sets the length of each processing region with respect to the direction of the created centerline such that the length continuously changes with the distance from the centerline.

9. A medical image display system according to claim 7, wherein the region setting means uses an assumed width of the luminal organs as the length of the processing region with respect to the direction of the curve.

10. A medical image display system according to claim 7, wherein the image creation means processes two-dimensional reconstructed image data and the set processing region having undergone predetermined processing such that the processing region can be identified.

11. A medical image display system according to claim 1, wherein the image creation means is connected to constriction-ratio computing means, wherein the constriction-ratio computing means detects a constricted portion of a luminal organ designated on the display.

12. A medical image display system according to claim 11, wherein the constriction-ratio computing means calculates the constriction ratio of the constricted portion of the luminal organ designated on the display.

13. A medical image display system according to claim 1, wherein the image creation means develops a plurality of curves in a three-dimensional coordinate space into straight lines and arranges them in parallel on a two-dimensional plane, and relates coordinates of each point on the plurality of curves in the three-dimensional coordinate space to two-dimensional coordinates of each pixel on the developed image.

14. A medical image display system according to claim 13, wherein the image creation means uses a pixel value of the three-dimensional image data at each point on the curves as a pixel value of each pixel on the developed image, which pixel corresponds to the point on the curves.

15. A medical image display system according to claim 1, further comprising curve-position moving means for moving the position of a curve displayed on the display apparatus, wherein
the image creation means creates the developed image on the basis of the curve after being moved.

16. A medical image display system according to claim 1, wherein the display apparatus displays a sectional image of the subject and the plurality of created curves such that the sectional image and the curves are superposed on each other.

17. A medical image display system according to claim 1, wherein the image creation means arranges in straight the intersections between the plurality of created curves and the centerline of the luminal organ designated from the plurality of selected luminal organs; and
the display apparatus displays the designated luminal organ straight on the basis of the created developed image.

18. A medical image display program embodied in a non-transitory medium which causes a computer to perform:

a sectional image display step of capturing a volume image of a subject by use of a medical image capturing apparatus and displaying a sectional image of the volume image;

a selection step of selecting a plurality of luminal organs on the displayed sectional image;

a designation point calculation step of calculating designation points for each position of centerlines corresponding to the plurality of selected luminal organs;

a curve creating step of creating a plurality of curves which cross the plurality of selected luminal organs from the calculated designation points;

a developed-image creation step of creating, on the basis of the pixel values of the volume images along the plurality of created curves, a two-dimensional developed image in which the plurality of selected luminal organs are depicted; and a developed-image display step of displaying the created developed-image.

* * * * *